(12) United States Patent
Kaizik et al.

(10) Patent No.: US 7,354,883 B2
(45) Date of Patent: Apr. 8, 2008

(54) CATALYST AND METHOD FOR THE PRODUCTION OF 1-OLEFINS FROM 2-HYDROXYLKANES

(75) Inventors: Alfred Kaizik, Marl (DE); Dietrich Maschmeyer, Recklinghausen (DE); Klaus-Diether Wiese, Haltern am See (DE); Wilfried Bueschken, Haltern am See (DE); Kurt-Alfred Gaudschun, Recklinghausen (DE)

(73) Assignee: OXENO Olefinchemie GmbH, Marl (DE)

( * ) Notice: Subject to any disclaimer, the term of this patent is extended or adjusted under 35 U.S.C. 154(b) by 0 days.

(21) Appl. No.: 10/576,302

(22) PCT Filed: Oct. 21, 2004

(86) PCT No.: PCT/EP2004/052607

§ 371 (c)(1),
(2), (4) Date: Apr. 19, 2006

(87) PCT Pub. No.: WO2005/058485

PCT Pub. Date: Jun. 30, 2005

(65) Prior Publication Data

US 2007/0043245 A1   Feb. 22, 2007

(30) Foreign Application Priority Data

Dec. 18, 2003 (DE) .................. 103 59 628

(51) Int. Cl.
*B01J 23/00* (2006.01)
*C07C 1/24* (2006.01)

(52) U.S. Cl. .................. 502/341; 502/349; 585/609; 585/639; 585/649

(58) Field of Classification Search .................. None
See application file for complete search history.

(56) References Cited

U.S. PATENT DOCUMENTS

| 4,328,373 | A * | 5/1982 | Strojny ................ 568/435 |
| 4,593,007 | A * | 6/1986 | Novinski .............. 501/105 |
| 4,681,979 | A | 7/1987 | Araki et al. .......... 585/640 |
| 5,204,308 | A * | 4/1993 | Lee et al. ............ 502/208 |
| 5,210,363 | A | 5/1993 | Sweeney .............. 585/640 |
| 6,015,928 | A | 1/2000 | Gubisch et al. |
| 6,184,424 | B1 | 2/2001 | Bueschken et al. |
| 6,239,318 | B1 | 5/2001 | Schuler et al. |
| 6,331,657 | B1 | 12/2001 | Kaizik et al. |
| 6,403,836 | B2 | 6/2002 | Kaizik et al. |
| 6,407,295 | B1 | 6/2002 | Kaizik et al. |
| 6,433,230 | B1 | 8/2002 | Bueschken et al. ... 568/388 |
| 6,482,992 | B2 | 11/2002 | Scholz et al. |
| 6,492,564 | B1 | 12/2002 | Wiese et al. |
| 6,500,991 | B2 | 12/2002 | Wiese et al. |
| 6,555,716 | B2 | 4/2003 | Protzmann et al. |
| 6,570,033 | B2 | 5/2003 | Rottger et al. |
| 6,603,047 | B2 | 8/2003 | Wiese et al. ......... 568/345 |
| 6,627,782 | B2 | 9/2003 | Kaizik et al. ........ 585/639 |
| 6,680,414 | B2 | 1/2004 | Knoop et al. |
| 6,720,457 | B2 | 4/2004 | Drees et al. |
| 6,818,770 | B2 | 11/2004 | Selent et al. |
| 6,924,389 | B2 | 8/2005 | Jackstell et al. |
| 6,956,133 | B2 | 10/2005 | Jackstell et al. |
| 6,960,699 | B2 | 11/2005 | Totsch et al. |
| 7,009,068 | B2 | 3/2006 | Schmutzler et al. |
| 7,109,346 | B2 | 9/2006 | Beller et al. |
| 7,166,757 | B2 * | 1/2007 | Fung et al. .......... 585/640 |
| 7,186,875 | B2 * | 3/2007 | Fung et al. .......... 585/640 |
| 7,205,447 | B2 * | 4/2007 | Levin et al. ......... 585/638 |
| 2004/0236133 | A1 | 11/2004 | Selent et al. |
| 2004/0238787 | A1 | 12/2004 | Wiese et al. |
| 2004/0242947 | A1 | 12/2004 | Beller et al. ......... 585/527 |
| 2005/0043279 | A1 | 2/2005 | Selent et al. |
| 2005/0065387 | A1 | 3/2005 | Beller et al. ......... 585/324 |
| 2005/0182277 | A1 | 8/2005 | Totsch et al. |
| 2005/0209489 | A1 | 9/2005 | Moller et al. |
| 2005/0234270 | A1 | 10/2005 | Kaizik et al. |
| 2005/0256281 | A1 | 11/2005 | Grund et al. |
| 2006/0036121 | A1 | 2/2006 | Kaizik et al. ........ 585/638 |
| 2006/0128998 | A1 | 6/2006 | Lueken et al. |
| 2006/0129004 | A1 | 6/2006 | Lueken et al. |
| 2006/0161017 | A1 | 7/2006 | Grass et al. |
| 2006/0183936 | A1 | 8/2006 | Grass et al. |
| 2006/0241324 | A1 | 10/2006 | Moeller et al. |
| 2007/0043245 | A1 | 2/2007 | Kaizik et al. |

FOREIGN PATENT DOCUMENTS

EP   0 219 609   4/1987

OTHER PUBLICATIONS

U.S. Appl. No. 10/562,454, filed Dec. 27, 2005, Krissmann et al.

(Continued)

*Primary Examiner*—Sikarl A. Witherspoon
(74) *Attorney, Agent, or Firm*—Oblon, Spivak, McClelland, Maier & Neustadt, P.C.

(57) ABSTRACT

The present invention relates to a process for preparing 1-olefins from 2-hydroxyalkanes by catalytic elimination of water under nonisomerizing conditions and to a catalyst which is particularly well-suited for this process and formally comprises yttrium oxide ($Y_2O_3$), zirconium dioxide ($ZrO_2$) and an alkali metal oxide and/or alkaline earth metal oxide.

20 Claims, No Drawings

OTHER PUBLICATIONS

U.S. Appl. No. 11/494,741, filed Jul. 28, 2006, Kaizik et al.
U.S. Appl. No. 10/576,302, filed Apr. 19, 2006, Kaizik et al.
U.S. Appl. No. 10/588,762, filed Aug. 8, 2006, Wiese et al.
U.S. Appl. No. 10/593,330, filed Sep. 19, 2006, Borgmann et al.
U.S. Appl. No. 10/584,492, filed Jun. 22, 2006, Ortmann et al.
U.S. Appl. No. 10/584,148, filed Jun. 22, 2006, Ortmann et al.
U.S. Appl. No. 11/574,063, filed Feb. 22, 2007, Nierlich et al.

* cited by examiner

CATALYST AND METHOD FOR THE PRODUCTION OF 1-OLEFINS FROM 2-HYDROXYLKANES

The present invention relates to a process for preparing 1-olefins from 2-hydroxyalkanes by catalytic elimination of water under nonisomerizing conditions and to a catalyst which is particularly well-suited for this purpose.

Owing to their reactivity, olefins are among the most important synthetic building blocks in organic chemistry. They are precursors for a large number of compounds, for example aldehydes, ketones, alcohols, carboxylic acids and halogen compounds. They are used in large quantities for producing homooligomers or cooligomers and homopolymers and copolymers, for example polyethylene or polypropylene.

Ethylene and propylene are prepared in large quantities through the world by steam cracking or catalytic cracking of hydrocarbons. This results in formation of appreciable amounts of $C_4$-olefins (isobutene, 1-butene and 2-butenes) and to a lesser extent $C_5$-olefins. Higher 1-olefins are usually produced by buildup reactions.

Ethylene can be oligomerized with the aid of Ziegler catalysts, giving a mixture of unbranched 1-olefins having an even number of carbon atoms.

Unbranched 1-olefins having even and odd numbers of carbon atoms can be prepared from ethylene by a variant of the SHOP process developed by Shell (Cornils and Herrmann, Applied Homogeneous Catalysis with Organometallic Compounds, vol. 1: Applications, pp. 251-256, Weinheim: VCH Verlagsges. 1996). This process comprises three reaction steps, namely ethylene oligomerization, isomerization, i.e. shifting of the double bonds, and cross-metathesis of the olefin mixture having internal double bonds with ethylene.

Dehydrogenation of straight-chain paraffins, for example by chlorination and subsequent dehydrochlorination, gives olefins having predominantly internal double bonds which can be converted by cross-metathesis into 1-olefins. The abovementioned processes all have the disadvantage that a number of 1-olefins are produced in each case.

Straight-chain 1-olefins having an even number of carbon atoms can be obtained, for example, from fatty alcohols by elimination of water. A disadvantage of this is the high price of the starting materials and the fact that essentially only fatty alcohols having from 12 to 18 carbon atoms are available in sufficient quantities.

A further possible way of preparing 1-olefins is to eliminate water from 2-hydroxyalkanes which are simple to prepare and thus inexpensive and mixtures thereof. The elimination of water is a β-elimination, i.e. the atoms of the water to be eliminated are bound to two adjacent carbon atoms. The elimination of water from 2-hydroxyalkanes forms 1-olefins (Hofmann product) and/or 2-olefins (Saitzew products) as primary product(s). The 2-olefins are thermodynamically more stable than the 1-olefin, and the olefins having double bonds located further in are even more stable. Under isomerizing conditions, a 1-olefin can be converted into olefins having internal double bonds until thermodynamic equilibrium is established. In the preparation of a 1-olefin, the formation of olefins having internal double bonds is disadvantageous for two reasons, namely because of the yield loss and because of the difficulty of separating off the 1-olefin since the boiling points of the isomeric olefins are close together.

The requirement for an industrial process for preparing 1-olefins from 2-hydroxyalkanes or from mixtures thereof is therefore a selective kinetically controlled elimination of water (formation of the carbon-carbon double bond between the first and second carbon atom) to form the target product while avoiding subsequent isomerization.

Owing to the ease of separating the reaction products from the reaction mixture, the elimination of water from 2-hydroxyalkanes is usually carried out in the gas phase or a mixed gas/liquid phase over solid catalysts in the temperature range from 200 to 500° C. Catalysts used are oxides of the alkaline earth metals, of aluminum, indium, gallium, of silicon, scandium, yttrium, lanthanum, titanium, zirconium, thorium and of the rare earths. It is also possible to use mixed oxides and combinations of some of the above oxides. In the case of some catalysts, a particular acidity is set by addition of alkali metal oxides.

The following catalysts are, for example, known from the scientific literature for elimination of water from 2-hydroxyalkanes:

$NiO/Al_2O_3$; $CuO/Al_2O_3$; $Al_2O_3$ (J. Mol. Catal. A. Chem. (1997), 121 (2-3), pp. 157-159);
$ZrO_2$; sulfated $ZrO_2$ (J. Mol. Cat. A. Chem (1997), 118 (1), pp. 88-89);
$Al_2O_3$; $Co_2O_3$; $ThO_2$; $In_2O_3$ (J. Catal. (1988), 110 (2), pp. 416-418);
$HfO_2/ZrO_2$ (J. Phys. Chem. (1980), 84 (1), 55-56);
$Al_2O_3/Na_2O_3$; ThO2 (J. Catal. (1981), 68 (2), pp. 383-387);
$ThO_2$ (J. Org. Chem. (1967), 32 (11), 3386-3389);
$La_2O_3$ (Z. Phys. Chem.(1985), 144, pp. 157-163);
$Ga_2O_3$ (J. Org. Chem. (1979), 44 (13), pp. 2142-2145);
$ThO_2$; $Al_2O_3$ (J. Org. Chem. (1972), 37 (8), pp. 1240-1244).

1-Olefins are formed from 2-hydroxyalkanes with selectivities of less than 90% over the abovementioned catalysts. Nonolefinic products such as ethers and ketones are also formed to a differing extent depending on the catalyst.

The patent literature likewise discloses a number of processes for preparing 1-olefins from secondary 2-alcohols.

EP 0 150 832 uses high-purity $ZrO_2$ containing less than 0.3% by mass of $SiO_2$ or $TiO_2$ as catalyst for eliminating water from secondary 2-alcohols. The selectivity of 1-olefin formation over this catalyst is not more than 91% at a conversion of 90%.

In EP 0 222 356, a $ZrO_2$ catalyst whose acidity has been modified by addition of alkali metal oxide or alkaline earth metal oxide is used for the same purpose. 4-Methyl-2-pentanol is converted with a selectivity of 92-94% into 4-methyl-1-pentene by means of these catalysts. By-products formed are internal olefins with a selectivity of 2-4% and ketones (by dehydrogenation) with a selectivity of 2-5%.

In the case of some applications, for example for use as comonomer, it is necessary for the olefin in question to have a high purity, i.e. having, inter alia, a low content of olefins having an internal double bond. The separation of a 1-olefin from its isomers having an internal double bond can frequently not be carried out at acceptable cost because of the small difference in the boiling points.

Since the ratio between 1-olefin formed and the sum of the isomers having an internal double bond is too small in the known processes for the dehydration of 2-alkanols, it is an object of the present invention to develop a process which in the elimination of water from 2-hydroxyalkanes and mixtures comprising 2-hydroxyalkanes provides not only a high selectivity for the formation of 1-olefins but also a high ratio of 1-olefins to the sum of their olefin isomers. This means that the 1-olefins formed must not isomerize by shifting of the double bond to internal olefins to a significant extent under the reaction conditions.

It has surprisingly been found that the use of a catalyst which formally comprises zirconium dioxide ($ZrO_2$) and yttrium oxide ($Y_2O_3$) and alkali metal oxide and/or alkaline earth metal oxide in the dehydration of secondary 2-alcohols under nonisomerizing conditions (i.e. use of a catalyst having a composition according to the present invention) enables olefins to be formed with a selectivity of up to 99% and 1-olefins to be obtained with a selectivity of up to 98.5%.

The present invention accordingly provides a catalyst which formally comprises zirconium dioxide ($ZrO_2$), yttrium oxide ($Y_2O_3$) and at least one oxide selected from among alkali metal oxides and alkaline earth metal oxides and in which the proportion of zirconium dioxide ($ZrO_2$) is from 80 to 99 parts by mass, the proportion by mass of yttrium oxide ($Y_2O_3$) is from 0.5 to 10 parts by mass and the proportion of alkaline earth metal oxide and/or alkali metal oxide is from 0.1 to 3 parts by mass.

The present invention likewise provides a process for preparing 1-olefins by catalytic dehydration (elimination of water) of alcohols at a temperature from 200 to 450° C., in which a catalyst according to the invention is used as catalyst and at least one secondary 2-alcohol is used as alcohol.

In addition, the present invention provides a composition which comprises at least one 1-olefin and is obtainable by the process of the invention and also provides for the use of such a composition according to the invention for preparing aldehydes and/or alcohols by hydroformylation of the 1-olefin present in the composition.

The process using the catalyst of the invention has the advantage that the as-dehydrated reaction mixture contains only a small proportion of by-products which cannot be recirculated to the dehydratation stage or a preceding stage, for example ethers derived from the starting material. The olefin fraction can comprise from 96 to 98.5% of 1-olefin, so that economical isolation of pure 1-olefin is possible. In the dehydration of secondary 2-alkanols (2-hydroxyalkanes) or of mixtures thereof, olefins can be formed with a selectivity of up to 99% and 1-olefins can be formed with a selectivity of from 95 to 98.5% by means of the process of the invention when the by-products formed by dehydrogenation, e.g. ketones, are recirculated to the dehydration according to the invention after hydrogenation to the starting alcohol.

The catalyst of the invention and the process of the invention are described below by way of example, without the invention being restricted to these illustrative embodiments. When ranges, general formulae or classes of compounds are indicated below, these are intended to encompass not only the respective ranges or groups of compounds which are explicitly mentioned but also all subranges and subgroups of compounds which can be obtained by taking out individual values (ranges) or compounds.

The catalyst of the invention, which formally comprises zirconium dioxide ($ZrO_2$), yttrium oxide ($Y_2O_3$) and at least one oxide selected from among alkali metal oxides and alkaline earth metal oxides, has a proportion of zirconium dioxide ($ZrO_2$) of from 80 to 99 parts by mass, a proportion by mass of yttrium oxide ($Y_2O_3$) of from 0.5 to 10 parts by mass and a proportion of alkaline earth metal oxide and/or alkali metal oxide of from 0.1 to 3 parts by mass or consists of these constituents.

The catalyst preferably has a proportion of zirconium dioxide ($ZrO_2$) of from 90 to 98 parts by mass, in particular from 93 to 96 parts by mass, a proportion by mass of yttrium oxide ($Y_2O_3$) of from 1.5 to 8 parts by mass, in particular from 3.5 to 6 parts by mass, and a proportion of alkaline earth metal oxide and/or alkali metal oxide of from 0.5 to 2 parts by mass, in particular from 0.5 to 1 parts by mass, or consists of these components.

The catalyst can comprise one or more oxide(s) from the group consisting of alkali metals and alkaline earth metals. The catalyst of the invention particularly preferably comprises an alkali metal oxide, in particular an alkali metal oxide selected from among potassium oxide and sodium oxide. The catalyst can, for example, be in the form of granules, tablets, cylinders, rings or extrudates. This is particularly advantageous when used in dehydration, since such shapes have a relatively low flow resistance.

A catalyst according to the invention can, for example, be prepared as follows: The preferred basis for the preparation of the catalyst of the invention can be a zirconium-yttrium mixed oxide. This can be prepared, for example, by coprecipitation of zirconium oxide and yttrium oxide or their hydroxides and subsequent dewatering of the precipitate. Another, preferred way of preparing zirconium-yttrium mixed oxide can comprise precipitating an yttrium-doped basic zirconium sulfate from an aqueous solution of zirconium and yttrium salts and, in a second step, converting it into a zirconium-yttrium oxide (hydroxide) by reaction with one or more bases. As base, preference is given to using ammonia or an ammonia derivative of carbonic acid (ammonium carbonate, ammonium carbamate, urea, urethanes) or a combination thereof.

The moist raw composition obtained in each case is preferably converted by drying at 110° C. to constant weight and subsequent calcination at temperatures up to 350° C., preferably 300° C., into a powder which formally comprises zirconium oxide ($ZrO_2$) and yttrium oxide ($Y_2O_3$). The calcination can be carried out in air. The calcination time is preferably from 3 to 10 hours, preferably from 3 to 7 hours.

Shaped bodies such as tablets, extrudates or pellets are preferably produced from the powder.

In the production of tablets, the above powder can be mixed with processing aids and binders, for example graphite and methylcellulose, and water. This mixture is pressed to form plates which are dried to constant weight at 110° C. The plates are broken up and passed through a sieve (mesh opening 0.8 mm) to give a free-flowing granular material which can be pressed in a tabletting machine to produce tablets, for example tablets having a thickness of 5 mm and a diameter of 5 mm.

Extrudates can be obtained by extruding a moldable mixture of zirconium oxide/yttrium oxide powder and water using a gear extruder.

Pellets, for example pellets having diameters of from 2 to 5 mm, can be produced from a moldable mixture, e.g. from the abovementioned mixture of zirconium oxide/yttrium oxide powder and water, in a pelletizing machine, for example a PO2 System Eirich with star whirler.

After all shaping procedures, the shaped bodies are preferably dried to constant weight at 110° C. and subsequently calcined at a temperature of from 500 to 700° C., preferably from 580 to 620° C. The calcination times can be from 2 to 7 hours, in particular from 3 to 5 hours.

The introduction of the alkali metal or alkaline earth metal component into the catalyst can be carried out before or after shaping. When the basic component is introduced before shaping, it is preferably incorporated as an aqueous solution into the composition to be shaped.

If the basic component is applied after shaping, this is achieved by impregnating or spraying the finished shaped body with, preferably, an aqueous solution of the base. Particularly in the case of impregnation, the average thickness of the outer zone in which the basic component is deposited can be set in a targeted manner by choosing a particular ratio of pore volume to solution volume. This is preferably followed by drying to constant weight at, preferably, 110° C. and calcination at a temperature of from 300 to 600° C., in particular at a temperature of from 350 to 450° C. The calcination time can be from 3 to 10 hours, in particular from 4 to 6 hours.

If the base is added before shaping, a catalyst in which the basic component or its subsequent product is uniformly distributed over the entire catalyst is obtained. When the basic component is introduced after shaping, a catalyst in which the basic component or its subsequent product is present mainly in the outer zones is formed.

The catalyst of the invention prepared in this way can be used in various catalytic reactions. The catalyst of the invention is particularly useful for the dehydration of alcohols.

In the process of the invention for preparing 1-olefins by catalytic dehydration (elimination of water) of alcohols at a temperature of from 200 to 450° C., a catalyst as claimed in any of claims 1 to 5 is used as catalyst and at least one secondary 2-alcohol is used as alcohol. It is possible to use a 2-hydroxyalkane, a mixture of isomeric 2-hydroxyalkanes or a mixture of 2-hydroxyalkanes having differing numbers of carbon atoms in the process of the invention.

In the process of the invention, secondary 2-alcohols having the general structure R—CH(OH)—CH$_3$ can be converted over the catalysts of the invention into the corresponding 1-olefins having the general structure R—CH=CH$_2$. Here, the group R is preferably a hydrocarbon group having from 3 to 25 carbon atoms. It can be aliphatic, linear or branched, alicyclic, alicyclic-aliphatic, aromatic or aromatic-aliphatic. Furthermore, methylene groups of these radicals can be replaced by oxygen. These compounds can be prepared, for example, by hydrogenation of saturated or unsaturated 2-ketones. The latter can easily be obtained by aldol condensation of an aldehyde with acetone. For example, 2-hydroxyoctane can be prepared by hydrogenation of oct-3-en-2-one which can in turn be prepared by condensation of pentanal with acetone.

Preference is given to using at least one alcohol containing from 3 to 27 carbon atoms, preferably from 8 to 16 carbon atoms and particularly preferably from 8 to 12 carbon atoms. Very particular preference is given to using 2-hydroxyoctane as alcohol. One or more alcohol(s) can be used as such or in admixture with further compounds, e.g. a diluent. Diluents which can be used are inert gases or gas mixtures, for example nitrogen, hydrogen, carbon monoxide, carbon dioxide, synthesis gas, methane or steam, or organic solvents which are inert under the reaction conditions and can easily be separated off from the reaction product mixture, e.g. by phase separation or distillation.

The dehydration can be carried out in the gas phase or a mixed liquid/gas phase. In the process of the invention, the dehydration is preferably carried out continuously or batchwise over suspended catalysts or particulate catalysts arranged in a fixed bed. The continuous dehydration is particularly preferably carried out over a fixed-bed catalyst.

In the continuous dehydration, it is possible to choose different process variants. The process can be carried out adiabatically, polytropically or virtually isothermally, i.e. with a temperature difference of typically less than 10° C., in one or more stages. In the latter case, all reactors, preferably tube reactors, can be operated adiabatically or virtually isothermally. It is likewise possible to operate one or more reactors adiabatically and to operate the others virtually isothermally. The dehydration is preferably carried out in a single pass. However, it can also be carried out with recirculation of product. In a single pass, the conversion of alcohol is preferably from 50 to 95%.

In single-pass operation, the WHSV (weight hourly space velocity) over the catalyst, in gram of starting material per gram of catalyst per hour, is preferably from 0.01 to 15 h$^{-1}$, particularly preferably from 0.1 to 10 h$^{-1}$, very particularly preferably from 0.5 to 5 h$^{-1}$.

The temperature in the catalyst bed is preferably from 200 to 450° C., in particular from 280 to 380° C. The dehydration can be carried out under reduced pressure, under superatmospheric pressure or under atmospheric pressure. The pressure (absolute) under which the dehydration is carried out is preferably from 0.1 to 25 bar. Preference is given to pressures of from 0.2 to 10 bar, particularly preferably from 1 to 5 bar.

To keep the selectivity of 1-olefin formation as high as possible, it can be advantageous to carry out the process in such a way that only a partial conversion of the alcohol used is achieved. The conversion can be adjusted, for example, via the Catalyst WHSV. As the space velocity over the catalyst increases, the conversion drops.

The reaction product mixture from the dehydration can be separated into an olefin fraction, an alcohol-containing fraction and one or more fractions comprising by-products such as ethers or carbonyl compounds, e.g. 2-ketones. The separation can be carried out, for example, by distillation. The olefin fraction obtained after the separation preferably comprises from 96 to >98% of 1-olefins. It can optionally be worked up to give an even purer 1-olefin. The alcohol-containing fraction comprising the unreacted alcohol is preferably returned to the dehydration. The 2-ketone (2-octanone) formed by way of example as by-product in the dehydration of 2-hydroxyalkane can be reused after hydrogenation to the corresponding alcohol and thus does not constitute a loss of useful material. The hydrogenation can be carried out in a separate hydrogenation apparatus. However, if the starting alcohols themselves are prepared by hydrogenation, it can be advantageous to feed the 2-ketones obtained as by-products into the hydrogenation preceeding the dehydration. This separation of the ketones from the mixture obtained in the dehydration, subsequent hydrogenation and recirculation of the alcohols obtained to the dehydration enables olefins to be formed with a selectivity of up to 99% and 1-olefins to be obtained with a selectivity of from 95 to 98.5% in the dehydration according to the invention of secondary 2-alkanols or of mixtures thereof.

The process of the invention makes it possible to obtain compositions which comprise at least one 1-olefin, preferably 1-octene, in a proportion of above 90% by mass, preferably above 95% by mass, particularly preferably above 97% by mass, in particular above 98% by mass. Further components which may be present in these compositions are further olefins other than 1-olefins. In the case of compositions comprising 1-octene as 1-olefin, the compositions can comprise, for example, 2-, 3- and 4-octenes.

The composition of the invention can be used for preparing aldehydes and/or alcohols by hydroformylation of the 1-olefin present in the composition. In particular, the composition of the invention can be used for preparing plasticizer alcohols, in particular for preparing nonanols such as isononanol. The compositions or olefins prepared by the process of the invention can be used as comonomers in the preparation of polyolefins. Furthermore, they can be used as starting materials for further organic syntheses.

The following examples are intended to illustrate the process of the invention without restricting its scope which is defined by the description and the claims.

EXAMPLE 1

Preparation of a Base-Free $ZrO_2/Y_2O_3$ Catalyst

A solution consisting of 624.7 g of zirconyl chloride hydrate ($ZrOCl_2*8H_2O$), 32.2 g of yttrium chloride hydrate ($YCl_3*6H_2O$) and 1800 g of deionized water was added at 50° C. to an aqueous ammonium sulfate solution prepared from 100 g of ammonium sulfate (($NH_4)_2SO_4$) and 3500 g of water over a period of one hour while stirring. The pH of the suspension formed was maintained in the range from 6.5 to 7.5 by simultaneous introduction of 380 g of an aqueous 20% strength by weight ammonia solution. The mixture was subsequently stirred for a further half hour at the same temperature. This reaction resulted in precipitation of an yttrium-doped basic zirconium sulfate which was separated off by means of a filter frit. The filter cake was washed with a total of 2000 g of deionized water, added in a plurality of portions, until it was free of chloride (until no chloride ions could be detected in the filtrate). The virtually chloride-free filter cake was added to a hot solution of 450 g of urea and 10 kg of deionized water at 85° C. over a period of one hour while stirring. The mixture was subsequently stirred for another 15 hours at the same temperature. After cooling to room temperature (20 to 25° C.), the solid was filtered off. The filter cake obtained was slurried in 2 kg of deionized water and filtered again. The solid on the filter was washed ten times with 1 kg each time of deionized water until it was free of sulfate (no sulfate detected in the filtrate). The virtually chloride- and sulfate-free filter cake was dried to constant weight at 110° C. It was subsequently calcined at 300° C. in a stream of air for 6 hours. The yield of yttrium oxide/zirconium oxide was 440 g. The mixed oxide formally consisted of 94.95% of zirconium oxide ($ZrO_2$) and 5.05% of $Y_2O_3$.

The mixed oxide obtained (440 g) was admixed with 300 g of deionized water and kneaded to form a moldable mixture. This composition was extruded by means of a gear extruder to form cylindrical shaped bodies having a length of 4-6 mm and a diameter of 1.25 mm. The extrudates were dried to constant weight at 110° C. and subsequently calcined at 400° C. for 5 hours. The finished shaped bodies (catalyst 1) had a BET surface area of 45 $m^2/g$ (determined according to the BET method by $N_2$ adsorption in accordance with DIN 66131) and a pore volume of 0.65 ml/g (determined by Hg porosimetry in accordance with DIN 66133).

EXAMPLE 2 (ACCORDING TO THE INVENTION)

Preparation of a $ZrO_2/Y_2O_3$ Catalyst With Sodium Oxide 200 g of the shaped bodies (catalyst 1 from Example 1) were impregnated at room temperature with a solution composed of 2.6 g of sodium hydroxide and 130 g of deionized water in a rotating drum (coating drum) by means of a spray nozzle. The alkalized shaped bodies were dried to constant weight at 110° C. and subsequently calcined at 400° C. for 5 hours. The shaped bodies (catalyst 2) formally contained 1% by mass of sodium oxide ($Na_2O$).

EXAMPLE 3 (COMPARATIVE EXAMPLE)

Dehydration Using the Catalyst Prepared in Example 1

The dehydration of 2-octanol to $C_8$-olefins in the presence of a catalyst in an electrically heated flow-through fixed-bed reactor was carried out using 2-octanol having a purity of >99.5% by weight from Fluka as starting material. The catalyst (catalyst 1) was a zirconium-yttrium mixed oxide (94.95% by weight of $ZrO_2$ and 5.05% by weight of $Y_2O_3$) as described in Example 1.

Before entering the reactor, the liquid starting material was vaporized at 220° C. in an upstream vaporizer. At a reaction temperature of 325° C. and a pressure of 1 bar in the reactor (diameter: 30 mm), 27.5 g/h of starting material were passed in gaseous form through 37.8 g (30 ml) of catalyst in extrudate form, corresponding to a WHSV of 0.7 $h^{-1}$. The gaseous product was cooled in a condenser and collected in liquid form in a glass receiver.

The GC analysis of the dehydration product is shown in Table 1, column 2. According to these results, a 2-octanol conversion of about 81% was achieved over catalyst 1 at 325° C. The product mixture comprised mainly $C_8$-olefin isomers (a total of 71.3% by weight) of which about 67.2% was the target product 1-octene. 2-Octanone and dioctyl ether are formed as by-products of the dehydration.

EXAMPLE 4 (ACCORDING TO THE INVENTION)

Dehydration Using the Catalyst According to the Invention

2-Octanol from Fluka was dehydrated in the presence of an $Na_2O$-modified $ZrO_2/Y_2O_3$ mixed oxide (catalyst 2) from Example 2 in a flow-through fixed-bed reactor as described in Example 3.

At two reaction temperatures of 325 and 350° C. and a pressure of 1 bar in the reactor, 28 g/h of 2-hydroxyoctane (2-octanol) in gaseous form were passed through 39.5 g of catalyst, corresponding to a WHSV of 0.7 $h^{-1}$. As in Example 3, the gaseous product was cooled in a condenser and collected in liquid form in a glass receiver. The GC analyses of the dissociation products over catalyst 2 according to the invention at 325° C. and 350° C. are shown in Table 1, columns 3 and 4.

As can be seen from Table 1, the 2-octanol is dissociated to the desired product 1-octene significantly more selectively with reduced formation of 3- and 4-octene isomers over the Na-modified $ZrO_2/Y_2O_3$ oxide (catalyst 2) compared to the unmodified $ZrO_2/Y_2O_3$ oxide (catalyst 1). At 325° C., a 2-octanol conversion of about 60% was achieved over catalyst 2. The product mixture contains a total of about 52.1% by weight of $C_8$-olefin isomers, of which about 97% is the target product 1-octene.

An increase in the reaction temperature from 325 to 350° C. at the same space velocity over the catalyst resulted in an increase in the 2-octanol conversion from 60 to about 88%. The product mixture from the 2-octanol dehydration at 350° C. contains a total of about 75.6% by weight of $C_8$-olefin isomers, of which about 94% is the target product 1-octene.

As can be seen from Table 1 (columns 3 and 4), the 2-octanol is dehydrated with high selectivity to the desired product 1-octene over catalyst 2 according to the invention. After the desired product and the by-products have been separated off by distillation, the unreacted 2-octanol can be recirculated to the dehydration reactor. The 2-octanone formed as by-product can be hydrogenated to 2-octanol.

TABLE 1

Results of GC analysis for Examples 3 and 4

| Component in % by weight | Example 3/ catalyst 1 T = 325° C. | Example 4/ catalyst 2 T = 325° C. | Example 4/ catalyst 2 T = 350° C. |
|---|---|---|---|
| 1-Octene | 47.97 | 50.65 | 70.95 |
| t-4-Octene | 0.35 | 0.00 | 0.00 |
| 3-Octene/c-4-octene | 2.10 | 0.02 | 0.08 |
| t-2-Octene | 9.17 | 0.95 | 2.75 |
| c-2-Octene | 11.75 | 0.59 | 1.84 |
| 2-Octanone | 7.24 | 8.55 | 12.24 |
| 2-Octanol | 17.89 | 38.96 | 11.44 |
| Dioctyl ether | 3.49 | 0.25 | 0.61 |
| Remainder | 0.04 | 0.03 | 0.09 |

The invention claimed is:

1. A catalyst comprising zirconium dioxide ($ZrO_2$), yttrium oxide ($Y_2O_3$) and at least one oxide selected from among alkali metal oxides and alkaline earth metal oxides and in which the proportion of zirconium dioxide ($ZrO_2$) is from 80 to 99 parts by mass, the proportion by mass of yttrium oxide ($Y_2O_3$) is from 0.5 to 10 parts by mass and the proportion of alkaline earth metal oxide and/or alkali metal oxide is from 0.1 to 3 parts by mass.

2. The catalyst as claimed in claim 1, wherein the proportion of zirconium dioxide ($ZrO_2$) is from 90 to 98 parts by mass, the proportion by mass of yttrium oxide ($Y_2O_3$) is from 1.5 to 8 parts by mass and the proportion of alkaline earth metal oxide and/or alkali metal oxide is from 0.5 to 2 parts by mass.

3. The catalyst as claimed in claim 2, wherein the proportion of zirconium dioxide ($ZrO_2$) is from 93 to 96 parts by mass, the proportion by mass of yttrium oxide ($Y_2O_3$) is from 3.5 to 6 parts by mass and the proportion of alkaline earth metal oxide and/or alkali metal oxide is from 0.5 to 1 part by mass.

4. The catalyst as claimed in claim 1, which comprises an alkali metal oxide selected from among potassium oxide and sodium oxide.

5. The catalyst as claimed in claim 1, which is in the form of granules, tablets, cylinders, rings or extrudates.

6. A process for preparing 1-olefins by catalytic dehydration (elimination of water) of alcohols at a temperature from 200 to 450° C., in which a catalyst as claimed in claim 1 is used as catalyst and at least one secondary 2-alcohol or a mixture thereof is used as alcohol.

7. The process as claimed in claim 6, wherein at least one alcohol having from 3 to 27 carbon atoms is used.

8. The process as claimed in claim 7, wherein 2-hydroxyoctane is used as alcohol.

9. The process as claimed in claim 6, wherein a mixture comprising further alcohols and/or hydrocarbons and also, if desired, a diluent is used.

10. The process as claimed in claim 6, wherein the dehydration is carried out in the gas phase or the mixed liquid/gas phase.

11. The process as claimed in claim 6, wherein ketones are separated off and hydrogenated from the mixture obtained in the dehydration and the alcohols obtained are recirculated to the dehydration.

12. The process as claimed in claim 6, wherein the reaction product mixture from the catalytic dehydration is separated into an olefin fraction, an alcohol-containing fraction and one or more fractions comprising by-products, and wherein the olefin fraction comprises from 96 to greater than 98% of 1-olefins.

13. The process as claimed in claim 6, wherein the catalytic dehydration of alcohols is at a temperature from 280 to 380° C.

14. The process as claimed in claim 7, wherein at least one alcohol having from 5 to 27 carbon atoms is used.

15. The process as claimed in claim 14, wherein at least one alcohol having from 6 to 16 carbon atoms is used.

16. The process as claimed in claim 15, wherein at least one alcohol having from 8 to 12 carbon atoms is used.

17. The process as claimed in claim 6, wherein the dehydration is carried out under a pressure from 0.1 to 25 bar.

18. The process as claimed in claim 17, wherein the pressure under which the dehydration is carried out is from 0.2 to 10 bar.

19. The process as claimed in claim 18, wherein the pressure under which the dehydration is carried out is from 1 to 5 bar.

20. The process as claimed in claim 6, wherein a composition is obtained; said composition comprising greater than 90% by mass of 1-octene.

* * * * *